United States Patent [19]

Neue et al.

[11] Patent Number: 5,374,755

[45] Date of Patent: Dec. 20, 1994

[54] LIQUID CHROMATOGRAPHY STATIONARY PHASES WITH REDUCED SILANOL INTERACTIONS

[75] Inventors: Uwe D. Neue, Ashland; Carsten L. Niederlaender, Milford; John S. Petersen, Acton, all of Mass.

[73] Assignee: Millipore Corporation, Bedford, Mass.

[21] Appl. No.: 916,775

[22] Filed: Jul. 17, 1992

[51] Int. Cl.$^5$ .......................... C07F 7/02; C08G 77/12
[52] U.S. Cl. ..................... 556/400; 556/419; 528/22; 528/31; 528/38; 210/198.2; 210/679
[58] Field of Search .................. 556/400, 419; 528/22, 528/31, 38; 55/386; 210/198.2, 679

[56] References Cited

U.S. PATENT DOCUMENTS

| | | | |
|---|---|---|---|
| 4,448,694 | 5/1984 | Plueddemann | 210/682 |
| 4,474,704 | 10/1984 | Sawicki | 260/429.7 |
| 4,812,512 | 3/1989 | Buendia et al. | 525/54.11 |
| 4,824,950 | 4/1989 | Barcza | 546/14 |
| 4,894,468 | 1/1990 | Wilchek et al. | 556/416 |
| 4,997,975 | 3/1991 | Lohmann et al. | 556/419 |

Primary Examiner—José G. Dees
Assistant Examiner—Porfirio Nazario
Attorney, Agent, or Firm—Andrew T. Karnakis; Paul J. Cook; Huw R. Jones

[57] ABSTRACT

Novel carbamate compounds, novel silylcarbamate compounds and novel reversed phase materials comprising a silica substrate modified with a modified novel silylcarbamate compound are disclosed which may, for example, be used as stationary phases for liquid chromatography applications. Attached to the carbamate group are several reversed or normal phase producing groups such as cyanoalkyl, tertiary butyl, dibutyl, octyl, dodecyl, tetradecyl, octadecyl or benzyl. The new stationary phases may be endcapped with a short chain alkyl silane. One particular advantage of these stationary phases is decreased interaction with basic samples due to shielding of the unreacted silanol groups on the silica surface. The new phases are particularly useful in the chromatographic analysis of basic samples or more generally for samples having an undesirable interaction with the unmodified silanols.

5 Claims, 8 Drawing Sheets

LIQUID CHROMATOGRAPHY STATIONARY PHASES WITH REDUCED SILANOL INTERACTIONS

FIELD OF THE INVENTION

The present innovation relates to new stationary phase materials and their use in HPLC (High Performance Liquid Chromatography). More particularly this invention relates to the synthesis of new silanes, their immobilization on silica and the use of the resulting phases in liquid chromatography.

HPLC is an efficient tool for separation of samples and its use is widespread throughout the analytical community. Very generally an HPLC separation is carried on with an instrument composed of solvent reservoirs, pumps, a mixing unit, an injection device, a chromatographic column, a detector and a data collecting device.

The sample is injected in a flow of an appropriate solvent going through the chromatographic column. The different components are separated in the column due to adsorption, absorption, size exclusion, ion exchange or other interactions with the packing material. The separated components are then detected in the detector. Some detectors which are commonly used include ultraviolet absorption, fluorescence, refractive index, conductivity, electrochemical and derivatization detectors. The data obtained is processed with an appropriate data module.

The most widely used packing materials are based on silica. By far the most common applications utilize a reversed phase silica, indicating that the silica is derivatized with an lipophilic agent such as chlorodimethyloctadecylsilane. The silica starting material is characterized by the presence of silanol groups on its surface. During the derivatization process with active silanes some of the silanols react with the derivatization agent.

Reversed phase packing materials for HPLC based on silica always contain unreacted silanol groups on the silica surface. Approximately 50% of the silanol groups remain unreacted during the hydrophobic derivatization of the silica. These residual silanol groups interact through ion exchange, hydrogen bonding and dipole/dipole mechanisms especially with basic or acidic samples. These remaining silanol groups create problems ranging from increased retention to excessive tailing and irreversible adsorption of the sample.

Common attempts to overcome the problem caused by the presence of silanol groups are based on modification of the silica itself such as the use of ultrapure silica, carbonized silica, coating of the silica surface with a polymeric composition, endcapping the residual silanol groups with a short chain alkyl silane and addition of suppressors such as long chain amines to the eluent. In practice none of these approaches is totally satisfactory.

A new approach was first described in European Patent Application 90302096.4 and Journal of Chromatography, Boguslaw Buszewski, Jutta Schmid, Klaus Albert, Ernst Bayer, 552 (1991), 415–427. Both sources demonstrate the solid phase reaction of surface modified silica bearing free amino groups with a "reversed phase producing" agent. The bare silica is first reacted with a monofunctional or trifunctional amino silane, which results in a coverage of the silica surface with free amino groups. These amino groups are then further derivatized with acid chlorides, phenylsulfonylchloride or alkylisocyanates in a second solid phase reaction. Both publications claim that the new phases are especially suited for the analysis of basic compounds.

The use of two consecutive solid phase reactions results in both cases in an undesirable inhomogeneous surface, containing a mixture of derivatized and underivatized amine groups. Furthermore the hydrolysis products of these phases possess ion exchange characteristics, which can influence negatively their chromatographic behavior.

SUMMARY OF THE INVENTION

The present invention provides novel carbamate compounds, novel silylcarbamate compounds and novel reversed phase materials comprising a silica substrate modified with a modified novel silylcarbamate compound. Attached to the carbamate group are several reversed or normal phase producing groups such as cyanoalkyl, tertiary butyl, dibutyl, octyl, dodecyl, tetradecyl, octadecyl or benzyl. The new stationary phases may be endcapped with a short chain alkyl silane. A typical synthesis example starting with octylamine and allylchloroformate is illustrated in the following steps 1 to 4.

Step 1: Synthesis of the carbamate

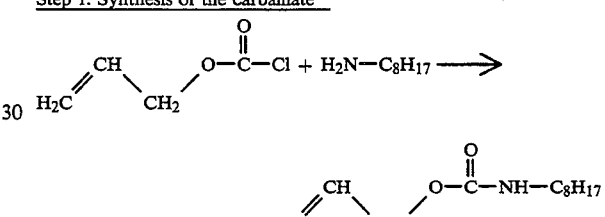

Step 2: Hydrosilyation

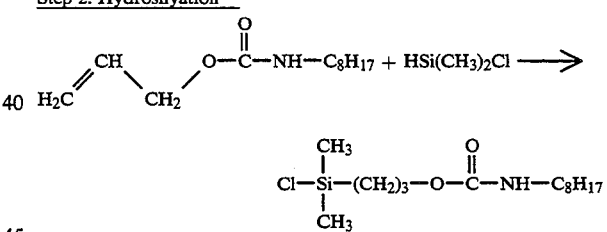

Step 3: Immobilization on a silica surface

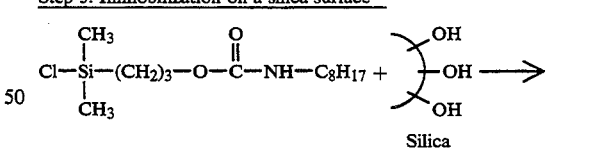

Step 4: Endcapping

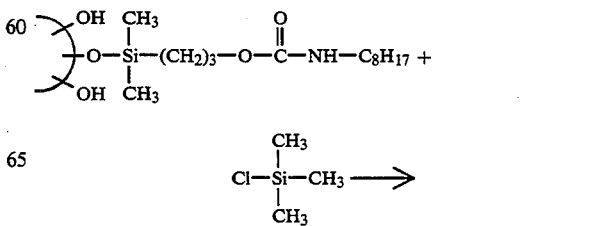

-continued

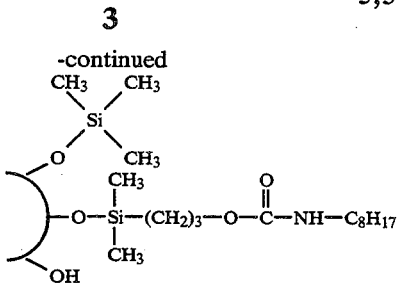

The new phases show decreased interaction with basic samples due to shielding of the unreacted silanol groups on the silica surface. The new phases are particularly useful in the analysis of basic samples or more generally for samples having an undesirable interaction with the unmodified silanols. The addition of suppressants to the buffer is no longer required to obtain symmetrical peak shapes for these compounds.

Furthermore the reversed phases of this invention have a uniform surface and neutral hydrolysis products which do not negatively influence the chromatographic behavior. Compared to the stationary phases mentioned in European Patent Application 90302096.4 and Journal of Chromatography, Boguslaw Buszewski, Jutta Schmid, Klaus Albert, Ernst Bayer, 552 (1991), 415–427 the hydrolysis of the novel phases results in neutral alcohol groups on the silica surface.

Hydrolysis of phases based on derivatized amines (prior art)

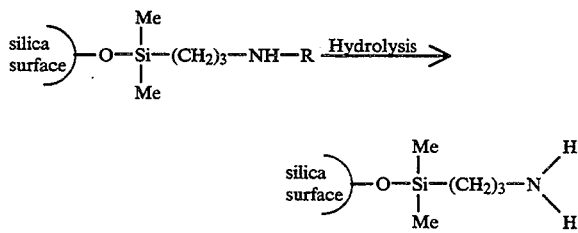

The regenerated free amino groups influence the characteristic of the phase through the introduction of new ion exchange properties, thereby possibly altering the chromatographic properties of the phase.

Hydrolysis of the novel stationary phases

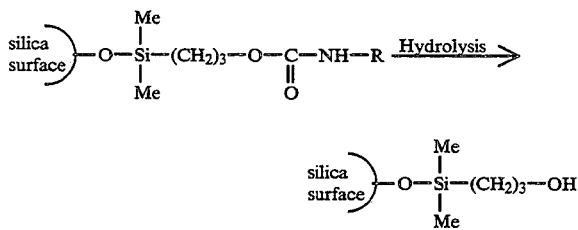

The newly generated hydroxy groups show no ion exchange properties over the pH range used in HPLC.

Furthermore the described derivatization of amino groups in a solid phase reaction results in a mixture of derivatized and not derivatized amine groups on the silica surface, since surface reactions almost never turn out complete. It is however desirable to achieve a highly homogeneous surface composition of stationary phases for use in HPLC. This can be done by the process described herein by reacting the silane, which already includes the polar carbamate group in a simple one step reaction with the silica surface silanols.

Silica surface reactions generally are difficult to control and it is therefore difficult to archive optimum reproducibility by the solid phase derivatization of the amine groups. The silanes of this invention allow a reproducible production of reversed phase materials with embedded polar carbamate groups.

DESCRIPTION OF SPECIFIC EMBODIMENTS

Figure 1A:
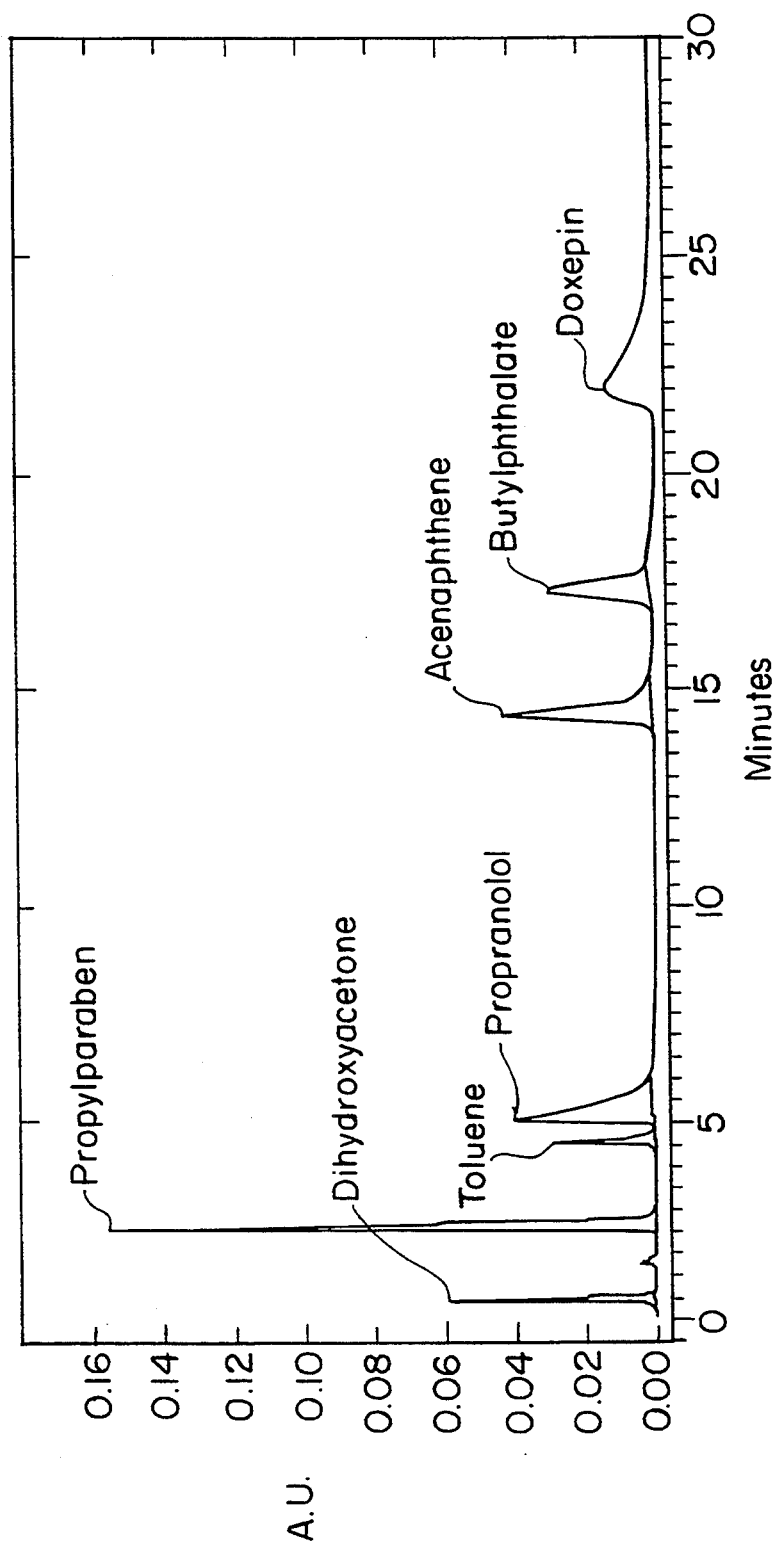
FIG. 1a and 1b show a chromatogram of neutral polar and basic test samples on a standard reversed phase compared to a novel shielded reversed phase material as described in example 25.

This invention provides a process for the reduction of silanol interactions from silica bonded phases in HPLC. A method of synthesizing normal and reversed phases on silica is also provided which provides novel stationary phases with better properties for their use in HPLC. A polar carbamate group is utilized to shield residual silanols on the surface. The carbamate group is attached to the silica particle across the oxygen site. A variety of normal or reversed phase producing ligands are attached to the nitrogen site of the carbamate. The present invention also provides a variety of new carbamates, whereof the silanes are descendents, and their synthesis. The new carbamates are generally described in formula I.

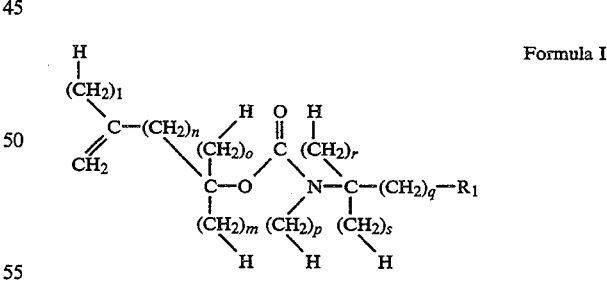

Formula I wherein l, m, o, r and s are 0 or 1; n is an integer from 0 to 3 and p is an integer from 0 to 4; q is an integer from 0 to 19 and R1 is cyano, hydrogen or phenyl.

More specifically the new carbamates are represented in the three following groups.

Group 1:

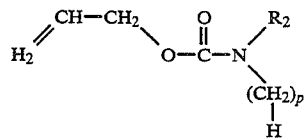

Group 2:

$$\begin{array}{c} CH_3 \\ | \\ H_2C=C-CH_2-O-\underset{\underset{O}{\|}}{C}-\underset{\underset{(CH_2)_p}{|}}{N}-R_2 \\ | \\ H \end{array}$$

Group 3:

$$\begin{array}{c} CH_3 \\ | \\ H_2C=CH-\underset{\underset{CH_3}{|}}{C}-O-\underset{\underset{O}{\|}}{C}-\underset{\underset{(CH_2)_p}{|}}{N}-R_2 \\ | \\ H \end{array}$$

$R_2$ = —H
 -alkyl ($CH_3$ to $C_{20}H_{41}$)
 —$(CH_2)_{1\ to\ 4}$-phenyl
 —$(CH_2)_{1\ to\ 4}$—CN
$p$ = 0, 1, 2, 3, 4

Examples of synthesized carbamates belonging to the different groups are as follows:

Group 1:

O-allyl-N-t-butylacarbamate $$H_2C=CH-CH_2-O-\underset{O}{\overset{\|}{C}}-\underset{H}{\overset{|}{N}}-\underset{CH_3}{\overset{CH_3}{\underset{|}{C}}}-CH_3$$

O-allyl-N-butylcarbamate $$H_2C=CH-CH_2-O-\underset{O}{\overset{\|}{C}}-\underset{H}{\overset{|}{N}}-(CH_2)_4-H$$

O-allyl-N-octylcarbamate $$H_2C=CH-CH_2-O-\underset{O}{\overset{\|}{C}}-\underset{H}{\overset{|}{N}}-(CH_2)_8-H$$

O-allyl-N-dodecylcarbamate $$H_2C=CH-CH_2-O-\underset{O}{\overset{\|}{C}}-\underset{H}{\overset{|}{N}}-(CH_2)_{12}-H$$

O-allyl-N-tetradecylcarbamate $$H_2C=CH-CH_2-O-\underset{O}{\overset{\|}{C}}-\underset{H}{\overset{|}{N}}-(CH_2)_{14}-H$$

O-allyl-N-octadecylcarbamate $$H_2C=CH-CH_2-O-\underset{O}{\overset{\|}{C}}-\underset{H}{\overset{|}{N}}-(CH_2)_{18}-H$$

O-allyl-N-benzylcarbamate $$H_2C=CH-CH_2-O-\underset{O}{\overset{\|}{C}}-\underset{H}{\overset{|}{N}}-CH_2-C_6H_5$$

O-allyl-N-cyanoethyl-N-methylcarbamate $$H_2C=CH-CH_2-O-\underset{O}{\overset{\|}{C}}-\underset{CH_3}{\overset{|}{N}}-(CH_2)_2-CN$$

O-allyl-N,N-dibutylcarbamate $$H_2C=CH-CH_2-O-\underset{O}{\overset{\|}{C}}-N\underset{CH_2-CH_2-CH_2-CH_3}{\overset{CH_2-CH_2-CH_2-CH_3}{\underset{}{\diagup}}}$$

Group 2:

O-(2methylallyl)-N-butylcarrbamate $$\begin{array}{c} CH_3 \\ | \\ H_2C=C-CH_2-O-\underset{O}{\overset{\|}{C}}-\underset{H}{\overset{|}{N}}-(CH_2)_4-H \end{array}$$

Group 3:

O-(1,1dimethylallyl)-N-butylcarbamate $$H_2C=CH-\underset{\underset{CH_3}{|}}{\overset{\overset{CH_3}{|}}{C}}-O-\underset{O}{\overset{\|}{C}}-\underset{H}{\overset{|}{N}}-(CH_2)_4-H$$

O-(1,1dimethylallyl)-N-octadecylcarbamate $$H_2C=CH-\underset{\underset{CH_3}{|}}{\overset{\overset{CH_3}{|}}{C}}-O-\underset{O}{\overset{\|}{C}}-\underset{H}{\overset{|}{N}}-(CH_2)_{18}-H$$

A wide variety of silanes is accessible by hydrosilylation of the new carbamates. Formula II shows the structure of these silanes.

Formula II $$R_5-\underset{\underset{R_4}{|}}{\overset{\overset{R_6}{|}}{Si}}-CH_2-\underset{\underset{(CH_2)_m}{|}}{\overset{\overset{(CH_2)_l-H}{|}}{C}}-(CH_2)_n-\underset{\underset{(CH_2)_p}{|}}{\overset{\overset{(CH_2)_o-H}{|}}{C}}-O-\underset{O}{\overset{\|}{C}}-N-\underset{\underset{(CH_2)_s}{|}}{\overset{\overset{(CH_2)_r-H}{|}}{C}}-(CH_2)_q-R_3$$

wherein $R_4$, $R_5$ and $R_6$ are $H_3C$, $H_3C(CH_2)$, $H_3CO$, $H_3C(CH_2)O$ or Cl wherein at least one is $H_3C(CH_2)O$, $H_3CO$ or Cl. l, m, o, r and s are 0 or 1; n is an integer from 0 to 3 and p is an integer from 0 to 4; q is an integer from 0 to 19 and $R_3$ is cyano, hydrogen or phenyl.

More specifically the silanes can be represented in the following group 4.

Group 4:

$$R_8\underset{\underset{R_9}{|}}{\overset{\overset{R_7}{|}}{Si}}-CH_2-\underset{CH_2}{\overset{CH_2}{\diagup\diagdown}}-CH_2-\underset{CH_2}{\overset{CH_2}{\diagup\diagdown}}-O-\underset{O}{\overset{\|}{C}}-\underset{\underset{(CH_2)_p}{|}}{\overset{\overset{R_2}{|}}{N}}-H$$

wherein $R_2$ is H, alkyl ($CH_3$ to $C_{20}H_{41}$), $(CH_2)_{1\ to\ 4}$-phenyl or $(CH_2)_{1\ to\ 4}$-CN; $R_7$ is $H_3C$, Cl or $H_3CO$; $R_8$ is $H_3C$, Cl or $H_3CO$; $R_9$ is $H_3C$, Cl, $H_3CO$. Wherein at least one of $R_7$, $R_8$ or $R_9$ is $H_3CO$ or Cl. p is 0,1,2,3 or 4.

Examples of newly synthesized silanes include:

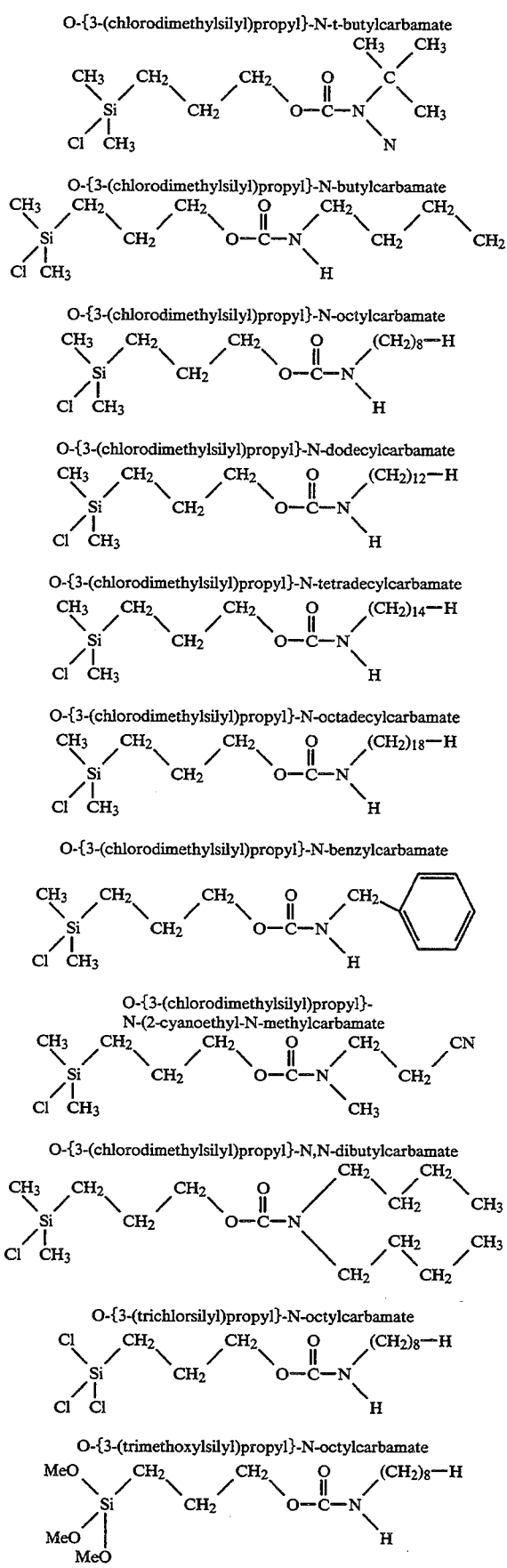

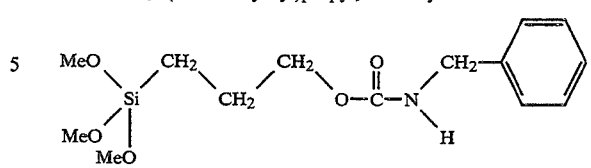

-continued
O-{3-(trimethoxysilyl)propyl}-N-benzylcarbamate

The different silanes are then allowed to react with a silica surface resulting in a coverage of 1 to about 4 μeq/m². Immobilization conditions depend on the silane used.

The following examples illustrate the present invention and are not intended to limit the same.

CARBAMATES OF GROUP 1

Example 1

Preparation of O-allyl-N-benzylcarbamate 71.12 g benzylamine were placed in a flask with 100 ml methylene chloride and 140 ml water. To the stirred mixture was slowly added 50 g allylchloroformate, during which the reaction temperature is not to exceed 20° C. (ice bath). Then 50 more g of allylchloroformate and 33.2 g NaOH in 150 ml water were added in parallel under the same conditions. After the addition was complete the mixture was stirred for 30 min at room temperature. The organic layer was separated, extracted with water (3×) and dried. The product was purified by distillation. Boiling point is 145° C. at 0.15 torr. ¹H NMR is consistent with the structure.

Example 2

Preparation of O-allyl-N-octylcarbamate

The procedure of example 1 was used except for 55 g octylamine, 64.5 g allylchloroformate and 21.4 g sodiumhydroxide. The amounts of water and methylene chloride were adjusted accordingly. Boiling point is 130° C. at 0.5 torr. ¹H NMR is consistent with the structure.

Example 3

Preparation of O-allyl-N-dodecylcarbamate

The procedure of example 1 was used except for 123.08 g dodecylamine, 100 g allylchloroformate and 33.2 g sodium hydroxide. The amounts of water and methylene chloride were adjusted accordingly. Boiling point is 175° C. at 0.2 torr. ¹H NMR is consistent with the structure.

Example 4

Preparation of O-allyl-N-tetradecylcarbamate

The procedure of example 1 was used except for 100 g tetradecylamine, 67.86 g allylchloroformate and 22.4 g sodiumhydroxide. The amounts of water and methylene chloride were adjusted accordingly. Boiling point is 150° C. at 0.15 torr in the kugelrohr distillation instrument. ¹H NMR is consistent with the structure.

Example 5

Preparation of O-allyl-N-tert.butylcarbamate

The procedure of example 1 was used except for 48.54 g t-butylamine, 100 g allylchloroformate and 33.2 g sodiumhydroxide. The amounts of water and methylene chloride were adjusted accordingly. Boiling point is 118° C. at 15 torr. ¹H NMR is consistent with the structure.

Example 6

Preparation of O-allyl-N-(2-cyanoethyl)-N-methylcarbamate

The procedure of example 1 was used except for 55.5 g (2-cyanoethyl)methylamine, 80 g allylchloroformate and 26.55 g sodium hydroxide. The amounts of water and methylene chloride were adjusted accordingly. Boiling point is 125° C. at 0.05 torr. ¹H NMR is consistent with the structure.

Example 7

Preparation of O-allyl-N,N-dibutylcarbamate

The procedure of example 1 was used except for 68.62 g dibutylamine, 80 g allylchloroformate and 26.55 g sodiumhydroxide. The amounts of water and methylene chloride were adjusted accordingly. Boiling point is 102° C. at 0.3 torr. ¹H-NMR is consistent with the structure.

Example 8

Preparation of O-allyl-N-octadecylcarbamate

An alternative method for the synthesis of the carbamates is the reaction of the different isocyanates with the appropriate alcohols. Examples for this type of reaction are given in this section.

500 g octadecylisocyanate were added to 666 g allylalcohol and heated to 75° C. over night. The excess allylalcohol was removed by distillation, the product was vacuum dried. ¹H-NMR confirmed the structure.

Example 9

Preparation of O-allyl-N-butylcarbamate 100 g butylisocyanate were added to 117.8 g allylalcohol. The mixture was stirred at room temperature over night and distilled. The product distilled over at 75° C. at 0.05 torr. /¹H-NMR confirmed the structure.

CARBAMATES OF GROUP 2

Example 10

Preparation of O-(2methylally)-N-butylcarbamate 100 g butylisocyanate were added to 145.5 g 2-methylallylalcohol. The mixture was stirred at room temperature overnight and distilled. The product distilled over at 85° C. and 0.03 torr. ¹H-NMR confirmed the structure.

CARBAMATES OF GROUP 3

Example 11

Preparation of O-(1,1dimethylallyl)-N-octadecylcarbamate

The procedure of example 8 was used except for 50.08 g octadecylisocyanate, 99.05 g 3-methylbut(1)en(-3)ol and 65° C. over night. The excess alcohol was removed by distillation, the product was vacuum dried. ¹H-NMR confirmed the structure.

Example 12

Preparation of O-(1,1dimethylallyl)-N-butylcarbamate 50 g butylisocyanate were added to 100 g 3-methylbut(1)en(3)ol. 10 g triethylamine were added. The mixture was stirred under reflux over night and distilled. The product distilled over at 65° C. at 0.03 torr. ¹H-NMR confirmed the structure.

Further confirmation of all new synthesized carbamates was obtained by elemental analysis (see table 1).

TABLE 1

| Carbamates | theor. % C | theor. % H | Group | % C | % H |
|---|---|---|---|---|---|
| O-allyl-N-benzylcarbamate | 69.10 | 6.85 | 1 | 69.52 | 7.03 |
| O-allyl-N-octylcarbamate | 67.57 | 10.87 | 1 | 67.56 | 11.22 |
| O-allyl-N-dodecylcarbamate | 71.33 | 11.60 | 1 | 71.47 | 11.76 |
| O-allyl-N-tetradecylcarbamate | 72.70 | 11.70 | 1 | 73.45 | 12.42 |
| O-allyl-N-tert.butylcarbamate | 61.12 | 9.62 | 1 | 60.67 | 9.42 |
| O-allyl-N,N-dibutylcarbamate | 67.57 | 10.87 | 1 | 67.48 | 10.81 |
| O-allyl-N-octadecylcarbamate | 74.73 | 12.26 | 1 | 74.89 | 12.3 |
| O-(1,1-dimethylallyl)-N-octadecylcarbamate | 75.53 | 12.41 | 3 | 76.16 | 12.49 |
| O-allyl-N-cyanoethyl-N-methylcarbamate | 57.13 | 7.19 | 1 | 57.34 | 7.26 |
| O-allyl-N-butylcarbamate | 61.12 | 9.62 | 1 | 60.81 | 9.67 |
| O-(2-methylallyl)-N-butyl carbamate | 63.13 | 10.01 | 2 | 63.02 | 9.91 |

A wide variety of silanes are accessible from the described new carbamates via hydrosilylation. Hydrosilylation of the double bond may be performed with trichlorosilane, trimethoxysilane, triethoxysilane, dichloromethylsilane, dichloroethylsilane, dimethoxymethylsilane, dimethoxyethylsilane, diethoxymethylsilane, diethoxyethylsilane, chlorodimethylsilane, chlorodiethylsilane, methoxydimethylsilane, methoxydiethylsilane, ethoxydimethylsilane, ethoxydiethylsilane or other related compounds.

The following examples are intended to illustrate and not to limit the present invention.

SILANES OF GROUP 4

Example 13

Preparation of O-{3-(dimethylchlorosilyl)propyl}-N-benzylcarbamate

To 50 g product of example 1 were added 100 mg hexachloroplatinic acid predissolved in 5 ml acetonitrile. 49.48 g chlorodimethylsilane were added and the mixture stirred at room temperature over night. The solution was heated to reflux for three hours to complete the reaction. The excess silane and the solvent were removed by distillation. The product was vacuum dried. ¹H—NMR confirmed the structure.

Example 14

Preparation of O-{3-(dimethylchlorosilyl)propyl}-N-octylcarbamate

The procedure of example 13 was used except for 80 g product of example 2 and 70.97 g silane. The amounts of hexachloroplatinic acid and acetonitrile were adjusted accordingly. ¹H—NMR is consistent with the structure.

Example 15

Preparation of O-{3-(dimethylchlorosilyl)propyl}-N-dodecylcarbamate

The procedure of example 13 was used except for 50 g product of example 3, 34.91 g silane and 100 ml dry toluene as solvent. The amounts of hexachloroplatinic acid and acetonitrile were adjusted accordingly. $^1$H—NMR is consistent with the structure.

Example 16

Preparation of O-{3-(dimethylchlorosilyl)propyl}-N-tetradecylcarbamate

The procedure of example 13 was used except for 60 g product of example 4, 38.2 g silane and 100 ml dry toluene as solvent. The amounts of hexachloroplatinic acid and acetonitrile were adjusted accordingly. $^1$H—NMR is consistent with the structure.

Example 17

Preparation of O-{3-(dimethylchlorosilyl)propyl}-N-tert.butylcarbamate

The procedure of example 13 was used except for 35 g product of example 5 and 42.13 g silane. The amounts of hexachloroplatinic acid and acetonitrile were adjusted accordingly. $^1$H—NMR is consistent with the structure.

Example 18

Preparation of O-{3-(dimethylchlorosilyl)propyl}-N-cyanoethyl-N-methyl carbamate The procedure of example 13 was used except for 40 g product of example 6 and 44.99 g silane. The amounts of hexachloroplatinic acid and acetonitrile were adjusted accordingly. $^1$H—NMR is consistent with the structure.

Example 19

Preparation of O-{3-(dimethylchlorosilyl)propyl}-N,N-dibutylcarbamate

The procedure of example 13 was used except for 80 g product of example 7 and 70.97 g silane. The amounts of hexachloroplatinic acid and acetonitrile were adjusted accordingly. $^1$H—NMR is consistent with the structure.

Example 20

Preparation of O-{3-(dimethylchlorosilyl)propyl}-N-octadecylcarbamate

The procedure of example 13 was used except for 400 g product of example 8, 214.1 g silane and 1500 ml dry toluene as acetonitrile. The amounts of hexachloroplatinic acid and acetonitrile were adjusted accordingly. $^1$H—NMR is consistent with the structure.

Example 21

Preparation of O-{3-(dimethylchlorosilyl)propyl}-N-butylcarbamate

The procedure of example 13 was used except for 50 g product of example 9 and 60.17 g silane. The amounts of hexachloroplatinic acid and acetonitrile were adjusted accordingly. $^1$H—NMR is consistent with the structure.

Example 22

Preparation of O-{3-(trimethoxysilyl)propyl}-N-benzylcarbamate

To 40 g product of example 1 were added 100 mg hexachloroplatinic acid in 5 ml acetonitrile. 38.27 g trimethoxysilane were added. The mixture was stirred at room temperature overnight, then heated to 65° C. for three hours to complete the reaction. The excess of reagent and solvent was removed by distillation. The product was vacuum dried. $^1$H—NMR confirmed the structure.

Example 23

Preparation of O-{3-(trimethoxysilyl)propyl}-N-octylcarbamate

To 33.34 g product of example 2 were added 100 mg hexachloroplatinic acid in 5 ml acetonitrile. 38.27 g trimethoxysilane were added. The mixture was stirred at room temperature overnight,

Example 24

Preparation of O-{3-(trichlorosilyl)propyl}-N-octylcarbamate

To 25 g product of example 2 in 100 ml dry toluene were added 100 mg hexachloroplatinic acid in 5 ml acetonitrile. 50 g trichlorosilane were added. The mixture was stirred at room temperature overnight, then heated to 65° C. for three hours to complete the reaction. The excess of reagent and solvent was removed by distillation. The product was vacuum dried. $^1$H-NMR confirmed the structure.

| Silane | theor. % C | theor. % H | % C | % H |
|---|---|---|---|---|
| O-{3-(dimethylchlorosilyl)-propyl}-N-benzylcarbamate | 54.62 | 7.05 | 54.35 | 7.21 |
| O-{3-(dimethylchlorosilyl)-propyl}-N-octylcarbamate | 54.60 | 9.82 | 54.11 | 9.82 |
| O-{3-(dimethylchlorosilyl)-propyl}-dodecylcarbamate | 59.39 | 10.52 | 59.94 | 11.18 |
| O-{3-(dimethylchlorosilyl)-propyl}-tert.butylcarbamate | 47.60 | 8.81 | 46.69 | 8.94 |
| O-{3-(dimethylchlorosilyl)-propyl}-N,N-dibutylcarbamate | 54.60 | 9.82 | 55.30 | 10.87 |
| O-{3-(dimethylchlorosilyl)-propyl}-N-octadecylcarbamate | 64.30 | 11.24 | 64.83 | 12.05 |
| O-{3-(dimethylchlorosilyl)-propyl}-N-butylcarbamate | 47.70 | 8.81 | 48.62 | 9.50 |
| O-{3-(dimethylchlorosilyl)-propyl}-N-cyanoethyl-N-methylcarbamate | 45.70 | 7.29 | 46.10 | 7.76 |
| O-{3-(trichlorosilyl)propyl}-N-octylcarbamate | 41.33 | 6.94 | 39.18 | 7.26 |
| O-{3-(dimethylchlorosilyl)-propyl}-N-dodecylcarbamate | 59.39 | 10.52 | 59.94 | 11.18 |
| O-{3-(trimethoxysilyl)propyl}-N-benzylcarbamate | 53.64 | 7.40 | 53.69 | 7.27 |
| O-{3-(dimethylchlorosilyl)-propyl}-N-tetradecylcarbamate | 61.45 | 11.10 | 61.38 | 10.70 |

The following examples show a variety of chromatographic separations. They show the chromatographic advantages of the new shielded phases over standard stationary phases.

Example 25

Figure 1B:
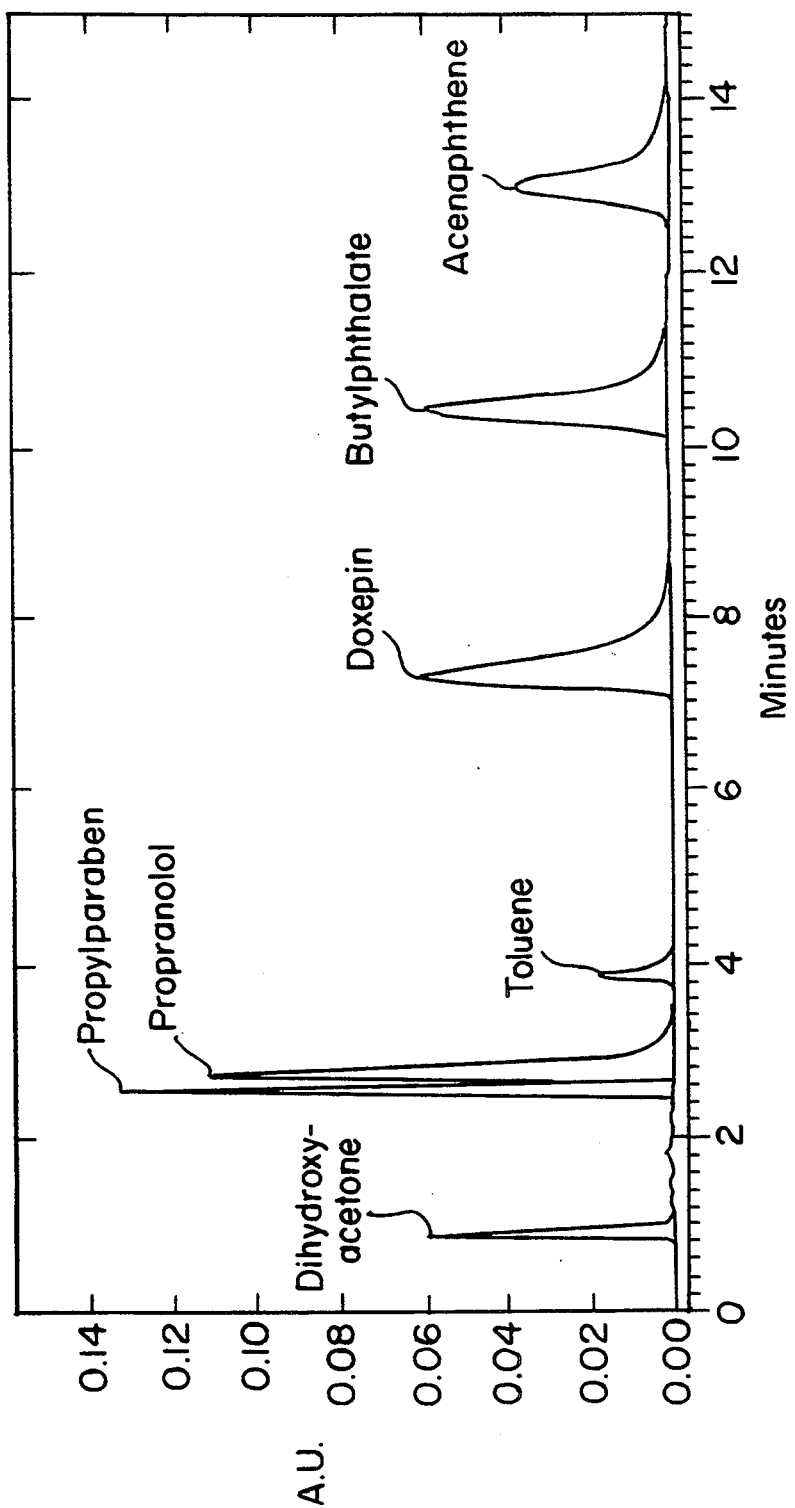

FIG. 1.a shows a liquid chromatogram of the test mixture obtained on a standard reversed phase material which is silica derivatized with chlorodimethyloctadecylsilane. FIG. 1a shows the tailing base peaks and the late elution of the basic samples. The influence of the underivatized silanol groups is strong. FIG. 1.b. shows a liquid chromatogram of the test mixture obtained on a shielded reversed phase material (silica derivatized with O-{3(dimethylchlorosilyl)propyl}-N-octadecylcarbamate. FIG. 1b shows the early elution of the basic samples and their symmetrical peak shapes.

The conditions for both chromatograms are identical: 3.9 mm by 15 cm column, 35 vol % 20 m phosphate buffer pH=7.00, 65 vol % MeOH, 1.5 ml/min, UV detection at 254 nm. The mixture contains dihydroxyacetone as an inert marker, propylparaben as an weak acid, toluene and acenaphthene as unpolar neutrals, propranolol and doxepin as hydrophobic bases and diutyl phthalate as a polar neutral.

Example 26

Figure 2A:
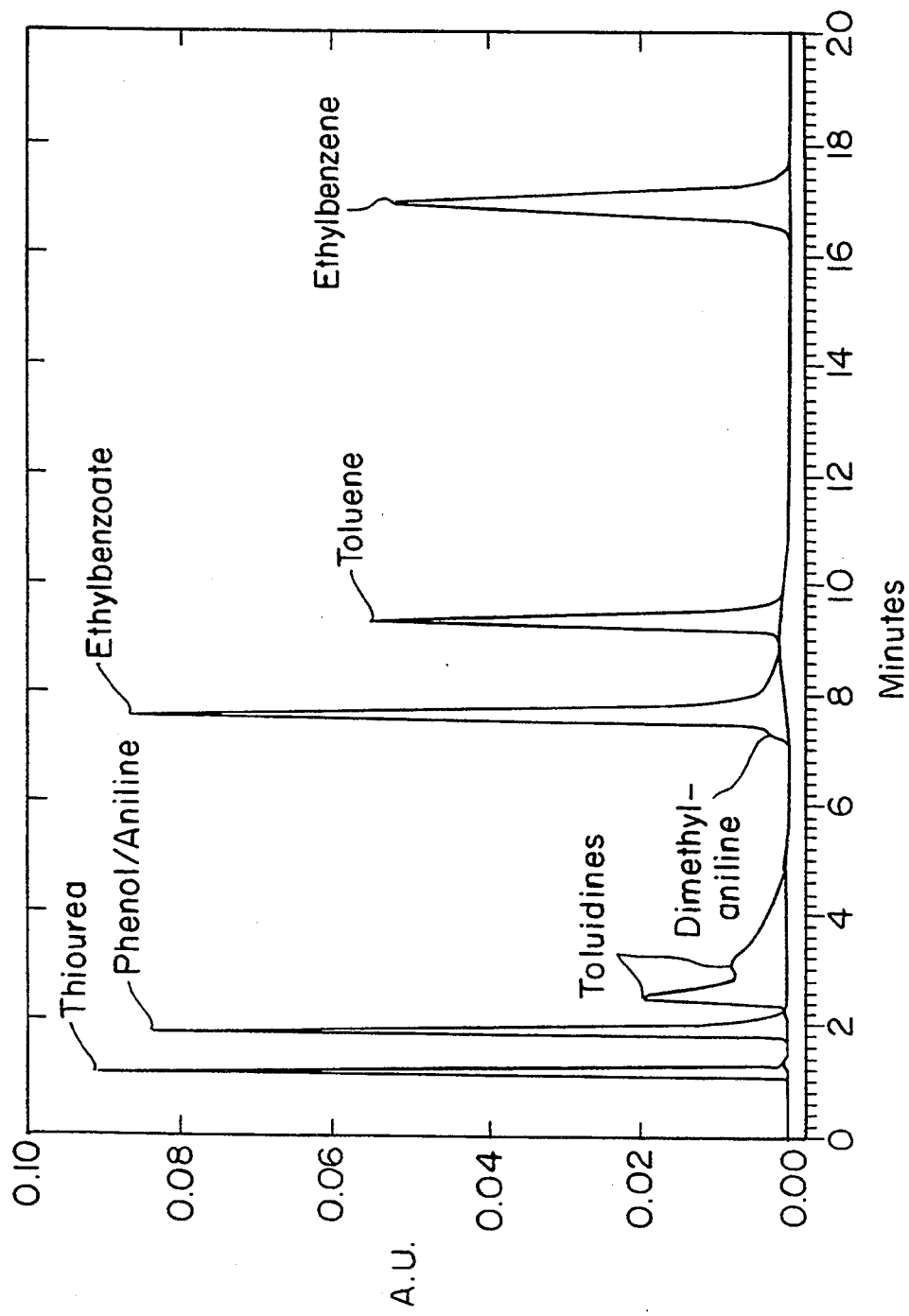
FIG. 2a and 2b show a chromatographic test described in Journal of Chromatography, Chromatographic characterization of silica based reversed phases, H. Engelhardt, H. Loew and W. Goetzinger, 544 (1991), 371–379. Phase 1 is a standard $C_{18}$ reversed phase. Phase 2 is a novel shielded $C_{18}$ reversed phase as described in example 26.
Figure 2B:
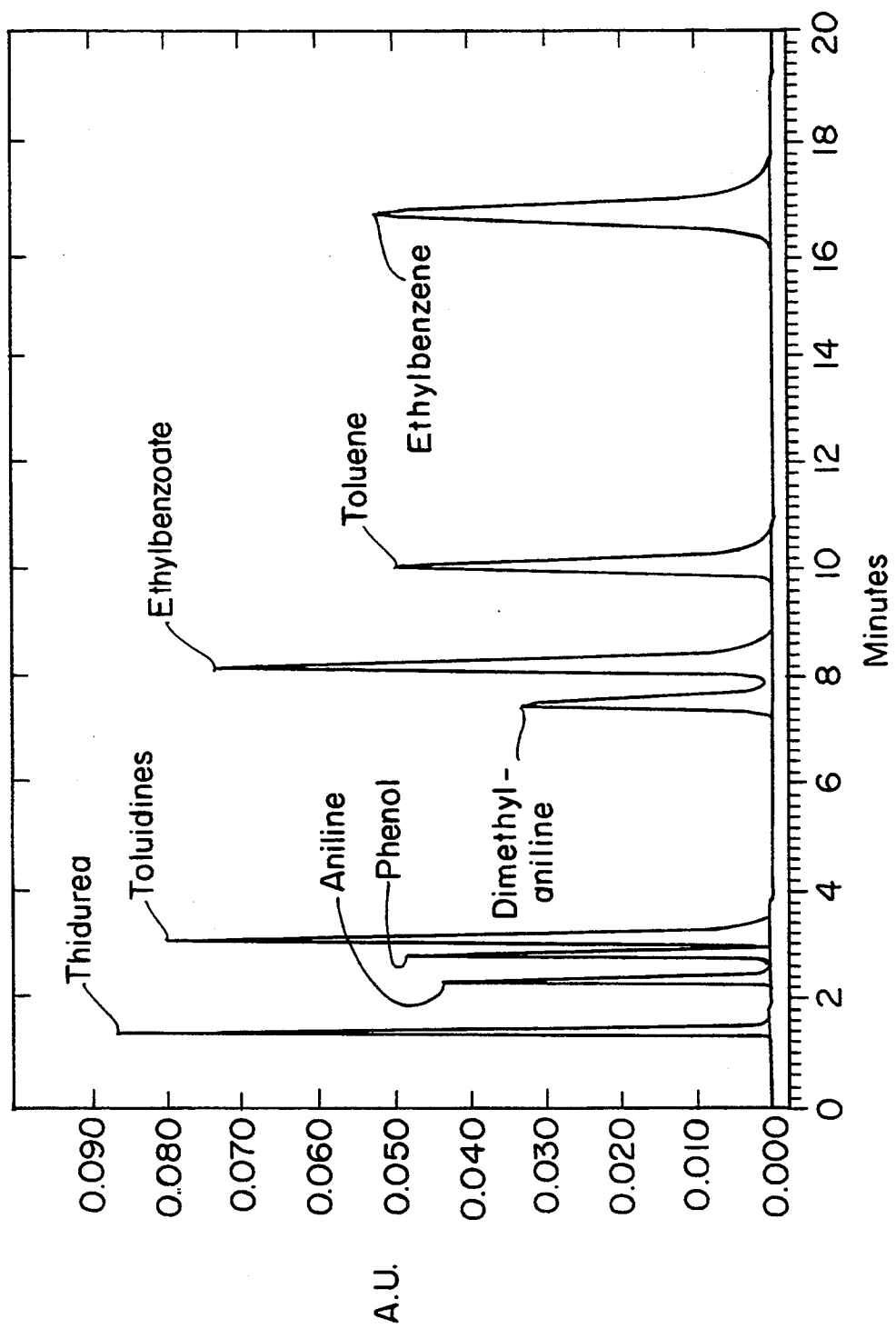

FIG. 2 shows a comparison of two endcapped $C_{18}$ phases on silica. Phase 1 is derivatized with chlorodimethyloctadecylsilane and then endcapped with hexamethyldisilazane (HMDS). Phase two is derivatized with O-{3(dimethylchlorosilyl)propyl}-N-octadecyl carbamate and then endcapped with HMDS. Basic samples are aniline, toluidines and dimethylaniline; neutral hydrophobic samples are toluene and ethylbenzene. Phenol and ethylbenzoate serve as as examples for polar samples. Eluent is methanol/water 49/51 w/w, flow rate is 1 ml/min.

The differences in the elution behavior of the sample show again the good shielding of the silanol groups obtained on the carbamate phase. The new phase fulfills all the parameters mentioned for a "good" reversed phase with low silanophile interactions: the toluidines are not separated (different pkA, same hydrophobicity) and the bases do not tail on the new phases.

Example 27

Figure 3A:
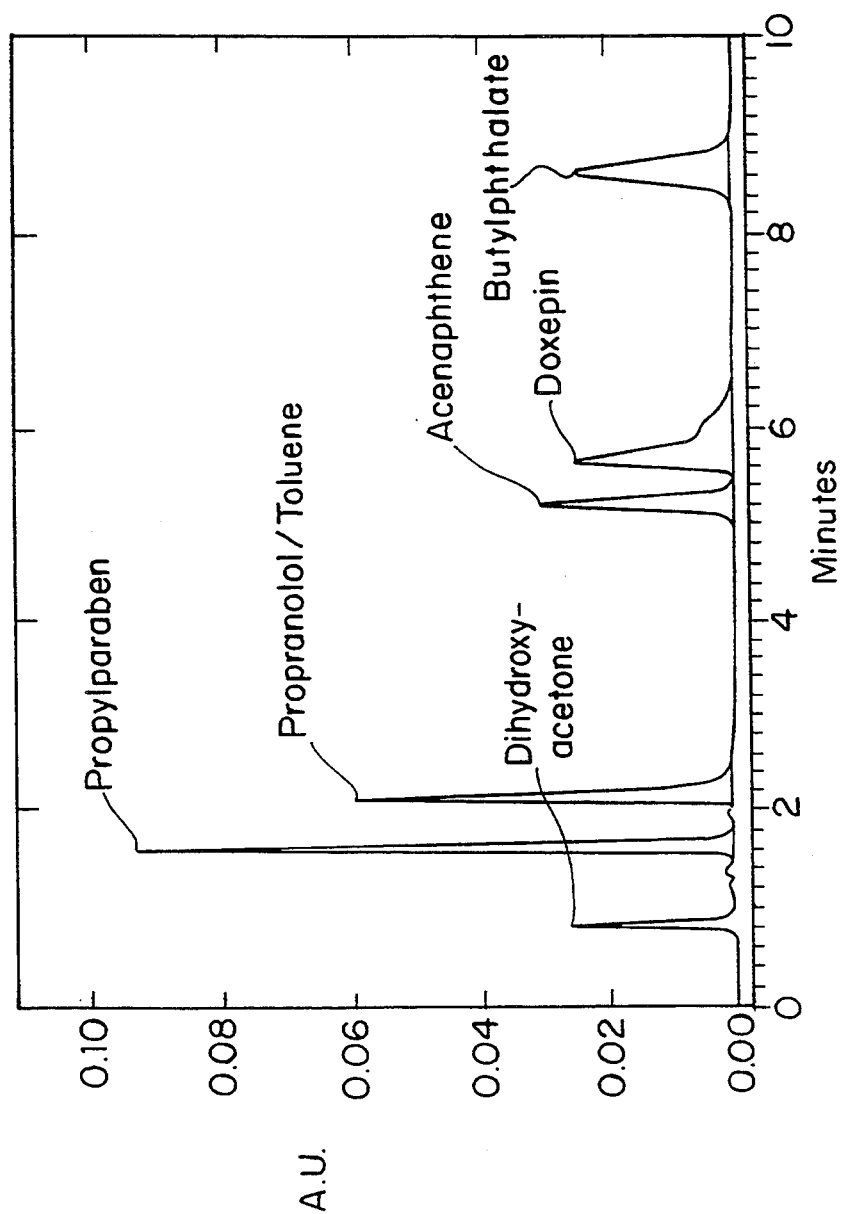
FIG. 3a and 3b show the test of FIG. 1 applied to a standard C8 reversed phase (endcapped) and to a novel shielded C8 phase (not endcapped). Even not endcapped the shielded phase yields better peak shapes for basic samples as described in example 27.
Figure 3B:
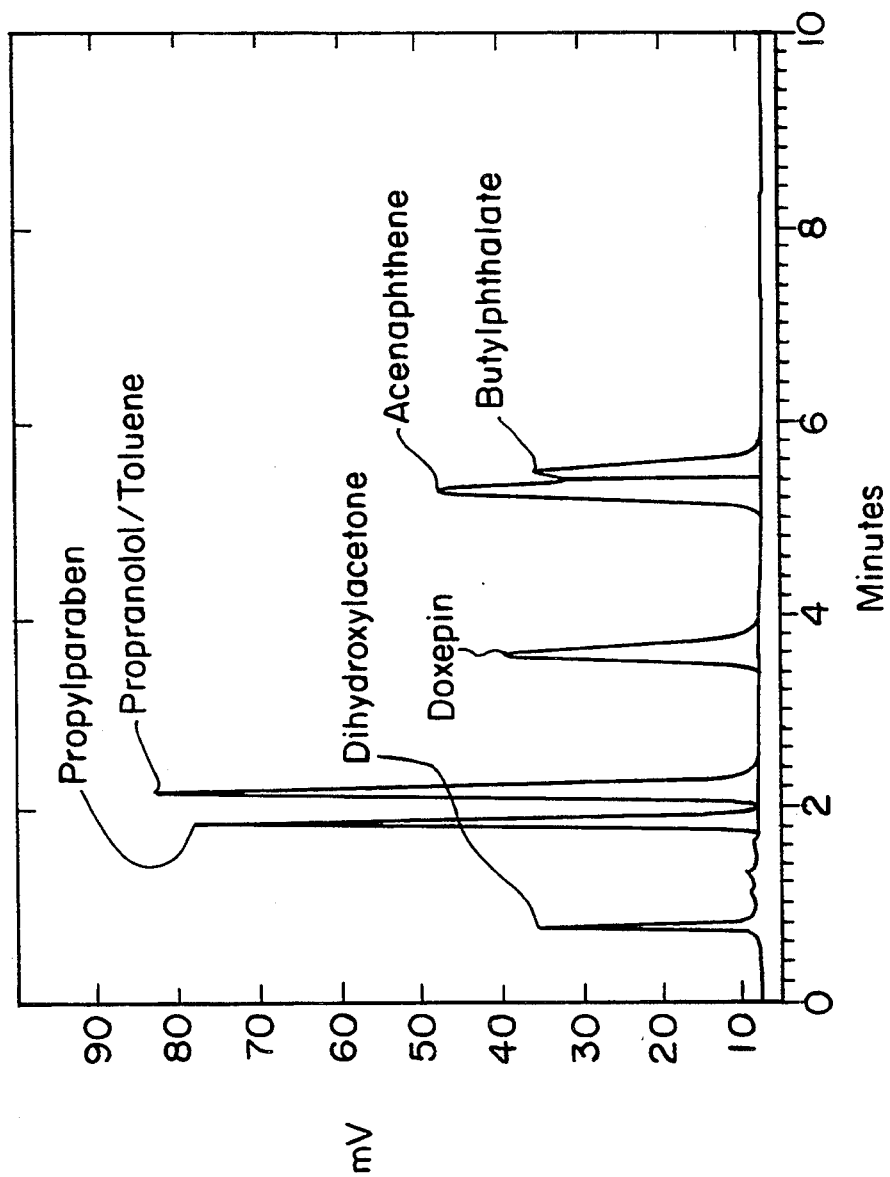

FIG. 3 shows a comparison of two $C_8$ phases on silica. The upper chromatogram is obtained on silica derivatized with monochlorodimethyloctylsilane (traditional $C_8$ reversed phase), which was thereafter endcapped with HMDS. The lower chromatogram was obtained on silica derivatized with O-{3(chlorodimethylsilyl)propyl}-N-octylcarbamate. This phase was not endcapped. However even without endcapping the new phase shows superior elution behavior for the basic samples in that the bases elute earlier and symmetrical). The elution pattern of unpolar hydrophobic samples comprising toluene, and acenaphthene is not influenced.

Example 28

Figure 4A:
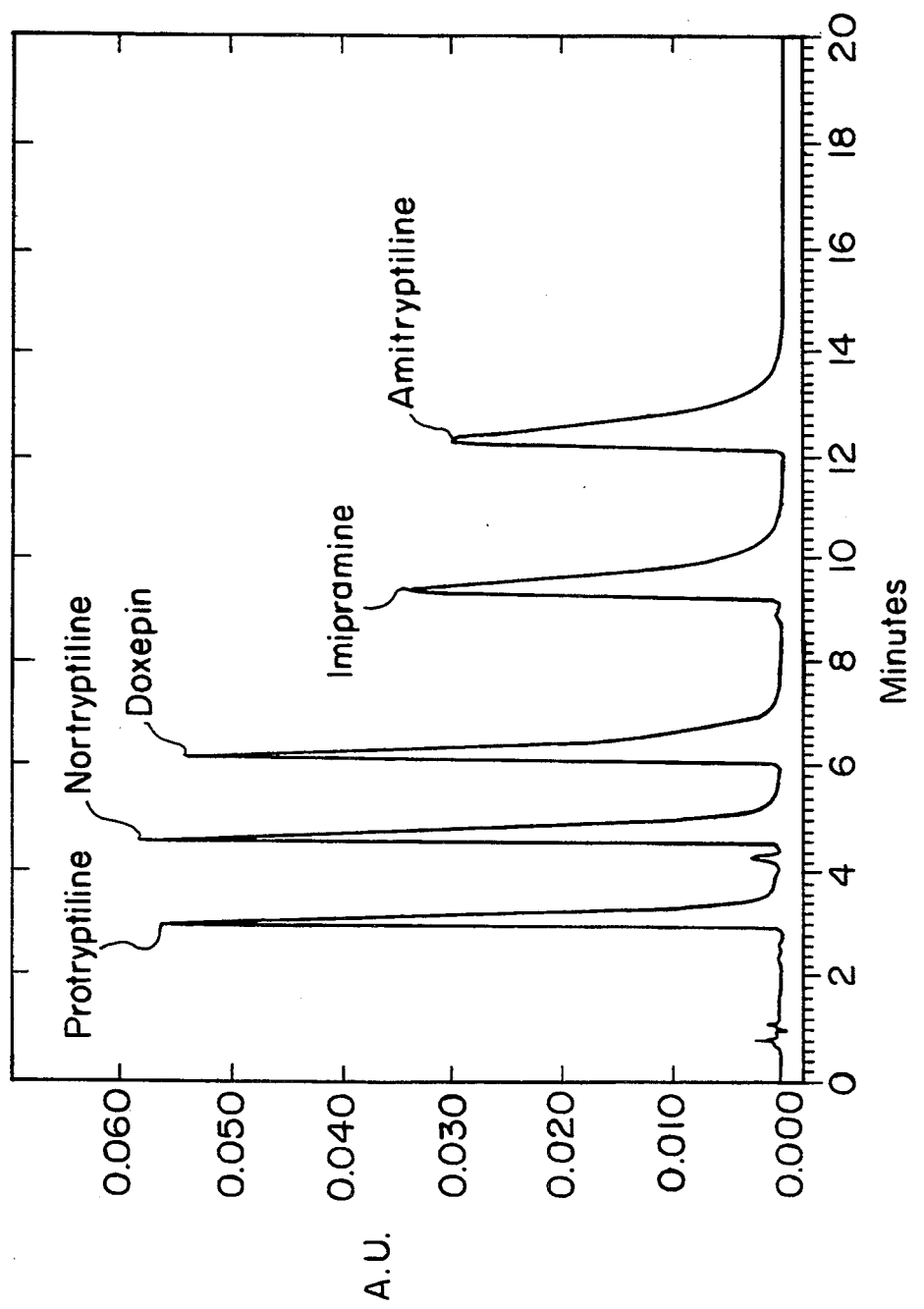
FIG. 4a and 4b show a separation of a mixture of commonly used antidepressants obtained on (1) a standard reversed phase and (2) a novel shielded phase as described in example 28.
Figure 4B:
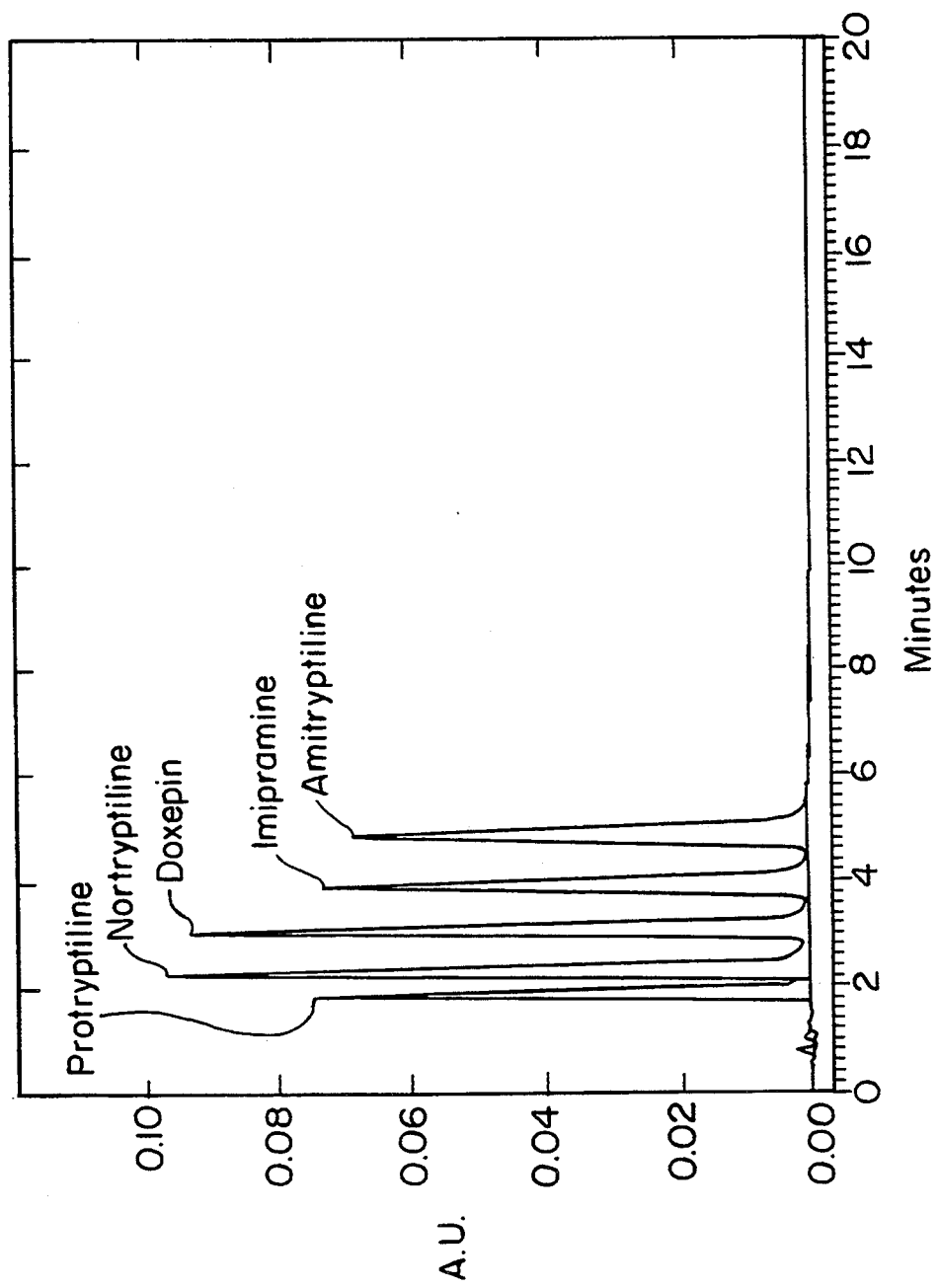

FIG. 4 shows an example of a separation of commonly used antidepressants. The drugs are all hydrophobic amines, which interact so poorly with residual silanols on standard reversed phase materials, that the separation is normally done on a cyanophase which causes problems such as the short life time of the stationary phase. Chromatographic conditions used are identical for both chromatograms. Eluent: 35 vol % 20 mM phosphate buffer pH=7.00 65 vol % MeOH, 1.5 ml/min, 5 µl injected of a drug mixture in MeOH/H2O, 3.9 mm by 15 cm column. With the novel shielded phases the separation is easily archived on a reversed phase without the need for suppressants in the buffer. 4.a. shows the separation obtained on a standard endcapped $C_8$ reversed phase. The peaks are tailing badly, quantification is difficult. 4.b. shows the separation on a new silanol shielded $C_8$ reversed phase. The peaks are symmetrical, the residual silanols are completely shielded. The basic drugs elute earlier. The following table shows an overview of the peak asymmetries on both phases, which illustrates again the superior properties of the new stationary phases. The asymmetry is measured at 4.4% peak height and squared.

| Sample | Asymmetry$^2$ Standard $C_8$ | Asymmetry$^2$ Shielded $C_8$ |
|---|---|---|
| Protryptiline | 10.2 | 2.6 |
| Nortryptiline | 16.8 | 2.7 |
| Doxepin | 21.5 | 1.4 |
| Imipramine | 20.1 | 1.5 |
| Amitryptiline | 20.3 | 1.6 |

The novel silanes of this invention were bonded on silica in a variety of ways depending on the silane, the silica and the desired phase properties.

Standard immobilization conditions for chlorosilanes include a concentration of the silane of 3 to 20 µeq/m$^2$ silica surface, reaction in an slurry of silica particles and an inert solvent for example methylene chloride or toluene at elevated temperatures and addition of an acid scavenger for example triethylamine, pyridine or imidazole to further the reaction.

Standard immobilization conditions for the alkoxysilanes include a concentration of the silane of 3 to 20 µeq/m$^2$ silica surface, reaction in a slurry of silica particles and an inert solvent for example toluene at elevated temperatures, addition of traces of water (0 to 2000 ppm) and possible addition of an catalytic reaction enhancer for example 5 mol % toluene sulfonic acid or triethylamine.

The described reactions result in new silica based stationary phases of formula III.

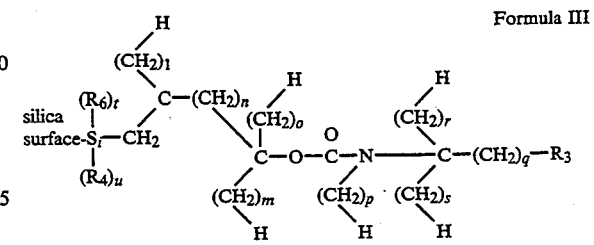

Formula III l, m, o, r and s are 0 or 1; n is an integer from 0 to 3 and p is an integer from 0 to 4; q is an integer from 0 to 19 and $R_3$ is cyano, hydrogen or phenyl; t and u are 0 or 1; $R_4$ and $R_6$ can be the same or different and are oxygen, methyl or ethyl.

The derivatized silica may be further reacted with a short alkylchain silane (endcapped) to further diminish the activity of the silanol groups.

Table 3 shows an overview of functionalized silica. The coverage obtained in the derivatization process with the appropriate silane is comparable to the one obtained with silanes without the embedded polar carbamate group. The silanes were immobilized on a variety of different silica with consistent results. The results shown here are obtained on a silica with 4 µm particle size, 40 Å pores and a surface area of 110 m$^2$/g.

TABLE 3

| Functional group | Leaving group of derivatizing silane | % C | % H | % N | Coverage (µeq/m$^2$) |
|---|---|---|---|---|---|
| phenyl | monochloro | 5.11 | 0.81 | 0.39 | 2.98 |

TABLE 3-continued

| Functional group | Leaving group of derivatizing silane | % C | % H | % N | Coverage (μeq/m²) |
|---|---|---|---|---|---|
| octyl | " | 5.95 | 1.25 | 0.50 | 3.23 |
| dodecyl | " | 7.18 | 1.41 | 0.44 | 3.02 |
| t-butyl | " | 4.51 | 0.99 | 0.48 | 3.41 |
| dibutyl | " | 5.76 | 1.18 | 0.45 | 3.11 |
| octadecyl | " | 7.46 | 1.57 | 0.33 | 2.35 |
| butyl | " | 4.58 | 1.03 | 0.51 | 3.47 |
| cyano | " | 4.48 | 0.91 | 1.02 | 3.39 |
| octyl | trimethoxy | 5.00 | 0.99 | 0.46 | 3.15 |
| phenyl | " | 4.54 | 0.71 | 0.41 | 2.86 |

The derivatized silica is packed in columns and ready for use in liquid chromatography.

We claim:

1. A surface modified silica of the formula III,

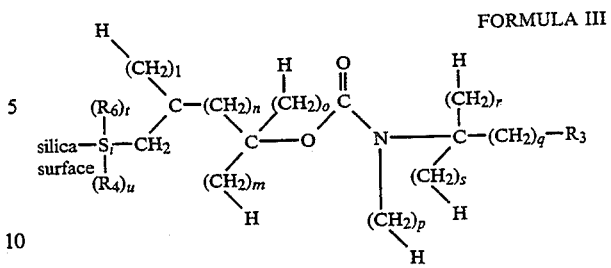

FORMULA III wherein l, m, o, r, s, t and u are 0 or 1, n is 0,1, 2 or 3 p is 0,1,2,3 or 4 and q is an integer from 0 to 19; $R_3$ is selected from the group consisting of hydrogen, alkyl, cyano and phenyl; and $R_4$ and $R_6$ are selected from the group consisting of oxygen, methyl and ethyl.

2. A silica having a surface to which is bonded 1 to 7 μeq/M² of $Si(R_7)_v(CH_2)_3O(CO)N(CH_2)_pH(CH_2)_qR_3$, wherein R7 is methyl or ethyl, v is 0,1 or 2, p is 0,1,2,3 or 4, q is an integer of 0 and 19 and $R_3$ is selected from the group consisting of cyano, phenyl and hydrogen.

3. The silica of any or of claims 1 or 2, when said modified silica surface is endcapped with a short alkyl chain silane.

4. The process of effecting chromatographic separations of a sample in a column which comprises:
packing said column with a modified silica of any one of claims 1 or 2, injecting a sample in said column and separating compounds in said sample by flow of a solvent through said column.

5. The process of claim 4 wherein said modified silica is endcapped with a short alkyl chain silane.

* * * * *